United States Patent [19]

Von Iderstein

[11] Patent Number: 5,624,374
[45] Date of Patent: Apr. 29, 1997

[54] INVOLUNTARY URINE CONTROL APPARATUS, SYSTEM AND METHOD

[76] Inventor: Irwin F. Von Iderstein, 136 Cotuit Bay Dr., Cotuit, Mass. 02635

[21] Appl. No.: 333,860

[22] Filed: Nov. 3, 1994

[51] Int. Cl.[6] .................................................. A61F 2/00
[52] U.S. Cl. ................................. 600/29; 128/DIG. 25
[58] Field of Search ............... 600/29–32; 128/DIG. 25

[56] References Cited

U.S. PATENT DOCUMENTS

| | | |
|---|---|---|
| 1,115,727 | 5/1914 | Tomkin . |
| 2,564,399 | 8/1951 | Trelkborg . |
| 3,642,004 | 2/1972 | Osthagen et al. . |
| 3,731,670 | 5/1973 | Loe . |
| 3,812,841 | 5/1974 | Isaacson . |
| 3,924,631 | 12/1975 | Mancusi, Jr. . |
| 3,926,175 | 12/1975 | Allen et al. . |
| 4,306,705 | 12/1981 | Svensson . |
| 4,679,546 | 7/1987 | Van Waalnijkvan-Doorn et al. . |
| 4,800,900 | 1/1989 | French . |
| 4,909,785 | 3/1990 | Burton et al. . |
| 4,994,020 | 2/1991 | Polyak . |
| 5,004,454 | 4/1991 | Beyar et al. . |
| 5,030,199 | 7/1991 | Barwick et al. . |
| 5,041,092 | 8/1991 | Barwick . |
| 5,112,306 | 5/1992 | Burton et al. . |
| 5,114,398 | 5/1992 | Trick et al. . |
| 5,140,999 | 8/1992 | Ardito . |
| 5,234,409 | 8/1993 | Goldberg et al. . |
| 5,513,660 | 5/1996 | Simon et al. ................ 600/29 |

Primary Examiner—Angela D. Sykes
Assistant Examiner—John P. Lacyk
Attorney, Agent, or Firm—Richard P. Crowley

[57] ABSTRACT

An involuntary urine control valve apparatus, system and method comprising a urine control valve adapted to be inserted a short distance into the distal end of the urethra of a subject, the control valve including a jacket which is fitted within the distal end of the urethra. The ball valve is a tension-biased, magnetic ball valve subject to move between open and closed position by an externally held magnet held by the subject near the jacket. The jacket includes a inflatable-deflatable collar in which is radially inflatable to stabilize the outer jacket within the urethra. The outer jacket includes an outwardly-extending flange at the other end, which extends about the urethral opening. The system includes a finger operated pump for the inflation of the collar in the outer jacket, to stabilize the outer jacket within the urethra. The system also includes a measuring tool kit for measuring urethral size to determine the correct size of the control apparatus to be employed.

23 Claims, 3 Drawing Sheets

1

INVOLUNTARY URINE CONTROL APPARATUS, SYSTEM AND METHOD

BACKGROUND OF THE INVENTION

There are a wide variety of structures and devices designed for the valving of bodily fluid, such as urine, and particularly to valve control devices for persons suffering from urinary incontinence. Urinary incontinence is a particularly long-recognized medical problem and relates to the inability of a subject to control voluntarily the elimination and function of the bladder, which problem can result from numerous causes.

While there are numerous apparatuses and methods for the valving of bodily fluids such as urine, it is desired to provide for a new and improved involuntary urine control apparatus, system and method, which avoids many of the difficulties associated with prior art apparatuses and methods of controlling urine flow.

SUMMARY OF THE INVENTION

This invention relates to an involuntary urine control valve apparatus, system and a method for the control of urine, which involuntary urine control valve apparatus is adapted to be inserted a short distance within the distal end of the urethra of a subject.

The invention relates to an involuntary urine control valve apparatus adapted to be inserted a short distance within the distal end of the urethra of a subject, and which valve apparatus comprises a urine control valve means, which valve means moves between an open, urine flow position which permits the flow of urine from a subject and a closed, urine stop position which prevents the flow of urine from a subject, the control of which valve means is controlled by the subject.

The urine control valve means includes an outer, generally cylindrical jacket having an external diameter which is adapted to fit slidably and comfortably within the interior of the urethra, having an inlet at the one end and an outlet at the other end, generally with the inlet and outlet aligned within the jacket. The jacket includes about the other end of the jacket a membrane collar type means, which is adapted to move radially between a fluid-inflatable position, which places the membrane in snug contact with the internal wall of the urethra of a subject in order to stabilize the jacket in position within the urethra and a collapsed, deflated position to permit the insertion into or withdrawal from the urethra of the jacket. The jacket includes a valve means, typically on the external one end thereof available to the subject, and a connecting passageway so as to supply or remove fluid to the collar membrane means, to provide for the movement of the collar means between said positions by the actions of a subject. The jacket includes an outwardly, radially extending flange from the one end and extending slightly outwardly from the open distal end of the urethra, generally and preferably curved and having a smooth, contoured, external surface so as to retain the jacket at the open distal end of the urethra.

The control valve means includes a head means, secured typically disposably at the outlet end of the jacket, with the head means having at least one outlet passageway and typically a central passageway surrounded by a plurality of other spaced-apart passageways to permit the flow of urine outwardly from the subject, and from the interior of the jacket. The control means also includes a tension-biased, magnetically-activated ball valve within the jacket, the ball valve adapted to move between a tension-biased, closed position to prevent the flow of urine from the inlet to the outlet and an open position against a valve seat, actuated by a magnet, to permit the flow of urine from the inlet to the outlet.

Typically, the valve seat is positioned generally adjacent and about the inlet end of the jacket at the other end, and the ball comprises a metal ball, typically with a thin coating of a biomedically-acceptable polymer, and which is tension-biased, such as by the employment of a spring of suitable tension. The tension-biased ball valve is characterized by sufficient tension in order to close the ball valve against the ball valve seat, and insufficient tension to prevent the opening of the ball valve if the bladder is full and requires urine release, and insufficient tension to prevent the movement of the magnetic ball valve from the ball valve seat to the open position on the ball valve seat unless it is activated by the influence of the magnetic force of an external magnet means.

The involuntary urine control apparatus also includes separate external means, such as a finger-operated fluid pump operated by the subject, to inflate the jacket collar membrane means into its inflatable, stabilizing position while the valve means, generally external at the one end of the jacket, also permits the deflation of the collar and membrane means, by the insertion of a small rod or pin into the valve to move the check ball away from the valve pump opening, releasing the fluid, to permit the removal of the jacket as required. The control apparatus also includes a separate, externally operated magnet means employed by the subject, and when placed adjacent the control valve means, permits the magnetic field of the magnet means to activate the magnetically-activated ball valve means and to move it from the closed to the open position as desired by the subject.

In a preferred embodiment, the urine control valve apparatus would have a generally disposable and removable head containing an outlet passageway for the passage of urine and which also contains a plurality of generally uniformly, longitudinally, slightly inwardly extending guide fingers about the head of the valve. The fingers may be inserted in the one or distal end of the valve jacket, and may be secured therein so that the head and guide fingers may be periodically removed as desired by the subject and replaced.

Thus, the involuntary urine control apparatus of the invention, with inlet and outlet openings for receiving, conducting and discharging fluids, typically urinary fluids from the urethra, is designed to hold its position within the distal end of the urethra of a subject and has a discharge outlet positioned slightly outside of the distal end or the opening of the urethra. The apparatus is held in a selected position a short distance within the end of the urethra by a precisely manufactured valve jacket, which includes a ball valve seat and a fluid control membrane or collar, which on inflation secures the valve jacket to the inner surface of the individual urethra wall, and wherein the valve jacket contains an outwardly extending flange positioned adjacent the distal end of the urethra, thereby stabilizing the urine control valve in the selected position.

The control device typically would include identical internal parts for both male and female users, and would comprise a urine control spring-guided ball valve, spring or tension-biased, necessary for a standard magnetic control operation to open and close the valve. Typically, the urine control spring guide attached to the head is threadably secured at the large end and secured to the head and spring guide fingers in an exact position in the distal end of the valve jacket for the tension-biased magnetic operation of the ball valve. The tension-biased ball valve maintains the valve closed against any fluid leakage, and any minor pressure from the bladder. However, the tension-biased ball valve is designed also to relieve any excess pressure around the bladder as a safety function, as well as to be operated by the externally operated magnet.

The valve jacket comprises, on its outer end or distal end extending around the circumference, an enlarged diameter, inflatably designed fluid control chamber extending from one to the other end from the external outer end to the membrane or collar apparatus, so that the inflated collar means provides for positively positioning the control apparatus for optimum control by a hand held permanent magnet by the subject. The elongated chamber is located in the outer surface of the cylindrical valve jacket, and the external diameter of the outer jacket is confined to an exact, precise diameter as by a urethral measuring tool, as hereinafter described.

The outer chamber, during the insertion into the urethra, has no volume of fluid within the collar or membrane means, as in a deflated position, so that the control apparatus outer chamber may be easily and comfortably inserted by the subject, so that the flange is positioned against the urethra opening. When the control apparatus is completely inserted within the urethra up to the flange, it may now be ready for the inflation of the collar or membrane means by slight pressure to fill the membrane collar with fluid, such as a liquid or gas, to make positive, absolute contact with the inside wall of the urethra, which operation is done by the subject, after having the initial fitting of the outer jacket determined by a physician or the subject himself, by means of a urethral diameter measuring tool, as hereinafter described.

Generally, a fluid is supplied to the outer chamber membrane collar from a small diameter capillary tube, connected to the outer chamber and encapsulated in the outer wall of the jacket, through a check valve to a point that: is positioned to connect with, for example, a finger pump on the discharge end of the flange of the jacket. The subject may use a finger pump or ball-type gas or liquid pump connected to the valve of the capillary tube passageway, so that the patient slowly pressurizes and inflates the membrane collar means to seal the other end of the jacket comfortably within the urethral walls, thereby completely stopping any flow or drip of urine past the jacket.

The control valve is not in flow position until the subject ascertains the need to urinate. Urination is accomplished by the subject simply placing a permanent magnet in a predetermined position for the magnetic field of the magnet to move the magnetically-activated, tension-biased ball valve off the ball valve seat, to a position against a ball valve stop within the spaced-apart spring guide fingers hence to permit urine flow, like a normal urinary function, from the inlet to the outlet, and to discharge from the distal end of the valve head. Urine flow is terminated by simply removing the permanent magnet, and the influence of the magnetic field from the magnetically-activated, tension-biased ball valve, so that the tension of the ball valve returns the ball valve to the ball valve seat, to stop urine flow.

For the insertion of the jacket within the distal end of the urethra, it is desirable to determine the individual subject's urethral diameter in order to properly fit the control apparatus. In one embodiment, the manufacture and use of measuring dowel tools are used to measure properly the individual subject's urethra. These tools are comprised of dowels, a temperature control chamber and sterilizing device as hereinafter described.

The urine control apparatus, system and method have numerous and significant advantages over prior art devices for the control of body fluids, and particularly urine control valves of the prior art. The control valve of the invention is precisely fitted and held directly to the inside diameter of the urethral wall a short distance from the distal end of the urethral opening; such as, for example, within one-half to one inch of the distal end. Therefore, there are no tubes, balloons or flushing tubes required. The control apparatus permits the subject to control the insertion, operation, withdrawal, dismantling, cleaning and disposal, and also permits the subject to apply antimicrobial cream to the surface of the control apparatus components. A removable valve head with the tension-biased ball valve can easily be removed, cleaned and re-inserted by the patient, and periodically removed and disposed of to employ a new, clean valve head. The control valve is simple in manufacture, operation and components, and comprises only four component parts; an outer jacket, a spring, a ball valve and a valve head for insertion into the jacket. The externally hand-held permanent magnet to operate the ball valve and an external fluidic pump are all controlled by the patient.

The control apparatus is also fitted precisely to the inside diameter of the urethra of a subject, and it is fitted with a deflatable and inflatable collar, so designed to be secured to the inside wall of the urethra in a gentle, comfortable manner, so as to handle pressure without movement, such as twice the pressure of the bladder urine, thereby stabilizing the control valve in its position. The control apparatus is so designed that the only surface of the control apparatus to come in contact with the patient's urine when the valve is in the closed, urine stop flow position is the end of the jacket and part of the ball valve.

If desired, the ball may be coated with an antimicrobial cream for insertion within the control apparatus. The control apparatus is so designed that the apparatus can be removed by the patient at any time, if required. The control apparatus and system is also simple to design, is inexpensive and may be made of light weight, medically and biologically acceptable polymer material. The ball valve typically comprises a metal, for example, a magnetic metal ball, generally stainless steel-coated with a thin coating of an inert plastic material, more particularly a fluorocarbon such as teflon.

Thus, the control valve would be coated with an antimicrobial cream and can be removed from the patient when needed. There is a minimum or very little chance of any microbial attack, since the only area of urine contact will be a small portion of the ball valve in the other end of the jacket within the urethra. Therefore, properly used and maintained, the control apparatus will remain sterile. The control apparatus is located in a convenient place to be controlled by the patient, that is typically a maximum of one inch in from the distal end of the urethra, to avoid any contact with the bladder. Generally and preferably, the jacket of the control device is precisely manufactured to the urethral size of the individual. The control device is easily operated by an external, hand-held, permanent magnet which is easily stored in the pocket or handbag for immediate use, and the inflation of the membrane collar means by the control valve is easily accomplished by a simple, finger-operated air pump, and the collar means deflated easily by insertion of a pin or small diameter rod to move the pump ball off the seat in the valve pump at the outer end of the jacket.

The procedure for inserting the urine control apparatus is quite simple, and usually includes having the subject wash his or her hands thoroughly with surgical soap, and then wash the genital area, and remove the control valve from a sterile packaging bag, wherein the subject coats the outer surface of the control apparatus and the ball valve with an antimicrobial cream, and then slowly inserts the control apparatus with the membrane or collar means in a deflated condition within the urethra until the flange reaches the outer end of the urethral opening. Upon completion of the insertion by the subject, the subject slowly pressurizes with the finger pump, the valve, pumping fluid through the inner capillary tube passageway into the membrane or collar means to place it in an inflated condition, until the jacket feels comfortably and securely in place within the urethra. With each pump operation, the subject holds the large flange at the end of the outer valve jacket and gently tries to remove the control device from the urethra. The subject may then continue pumping when there is a slight tension pulling the control apparatus until the control apparatus feels tightly positioned and stabilized within the urethra.

In another aspect of the invention, the urine control apparatus requires the precise measurement of the subject's urethra, which may be accomplished by any technique; however, a specially designed measuring tool and procedure has been developed to fit individually the subject's urethra. The urethral measuring tool kit is designed to provide a plurality of dowels, each dowel designed to be inserted into a proper depth within the urethra to determine the size for maximal operation. The measuring tools should be able to measure properly each subject's urethra over the entire length of the urine control valve apparatus, but generally not greater than about one inch from the distal end of the urethra. The dowels of the tool kit should be selected and inserted in a sequence to be slowly enlarged to a proper fit and comfortable feel to the subject before actually forming and inserting the outer jacket.

Generally, the subject must be able to remove the measuring tool dowel as if it were the uninflated valve jacket, to install it with ease and comfort within the urethra. Thus, after the measurement of the urethral wall has been determined, the measurement will be employed to form the outer jacket which will enclose and seal the ball valve inside the jacket.

The urethra is malleable, pliable, flexible and very sensitive to heat and cold, and will tend to stretch or return to its normal size. It is therefore necessary for all tools and instruments to be kept, maintained and used at body temperature. In addition, the measuring tools and dowels should be highly polished and have a smooth surface over their entire surface, and insertion of the measuring tools or dowels should be done with the same tool with which the outer valve jacket will be installed, and the measurement tools should be sterilized during handling periods.

The measuring tool kit generally comprises 15 to 20, or more or less as desired, cylindrically shaped dowels, generally up to about an inch long, for example, 0.750 inches, along with diameters ranging from 0.25 inches diameter to 0.335 inches in diameter and generally are increased in selected increments, such as 0.05 inch diameters and stored in sterile packages at body temperature. Once the exact diameter of the urethra is determined, the subject may then install the properly dimensioned outer valve jacket within the distal end of the urethra.

Measuring tools or dowels of the urethra measuring kit generally comprise a smooth, round, biocompatible surface, made of a biomedically-acceptable material, with a slightly diameter-enlarged cylindrical end, a short, generally cylindrical end extending essentially from one end of the dowel, the other end of the dowel being a smooth, curved surface, typically a handle, generally comprising a flange similar to the flange end employed in the outer valve jacket, having an outwardly curved surface, so as to mimic the other flange of the valve jacket.

While the urine control valve apparatus has been described in connection with the insertion in the end of the urethra for urine control, it is recognized that the control valve may be used for the control for other bodily fluids by insertion in other bodily fluid flow passages where subject control of bodily fluids is desired.

The urinary incontinence control apparatus and invention may be easily employed with both male and female subjects, but will be described for the purposes of illustration only in connection with certain illustrated embodiments; however, it is recognized that those persons skilled in the art may make various modifications, changes, improvements and additions to the illustrated control valve system and method without departing from the spirit and scope of the invention.

DESCRIPTION OF THE EMBODIMENTS

Figure 1:
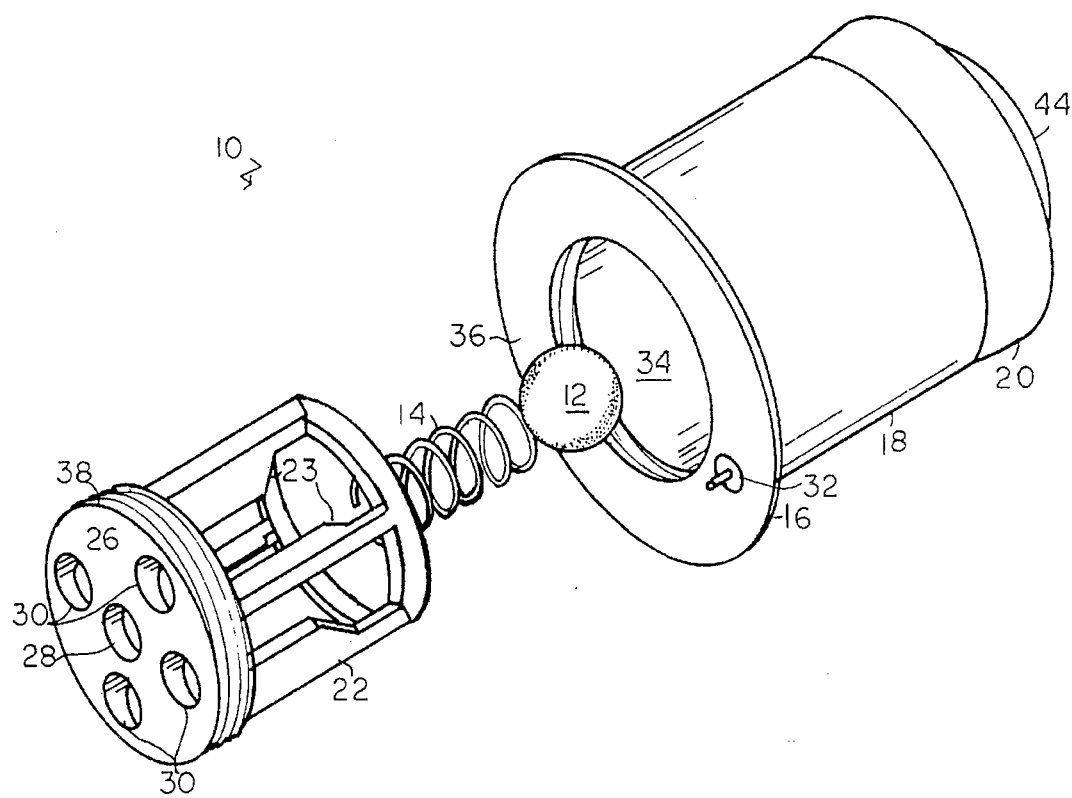
FIG. 1 is an exploded perspective view of the urine control valve of the invention.

As illustrated, FIG. 1 shows the involuntary urine control apparatus of the invention in an exploded perspective view, with the teflon-coated metal ball 12 positioned to rest on one end of the tension-biased spring 14 extending within the valve chamber 34 of the valve jacket 18. The other end of the spring 14 rests within the four spaced-apart, inwardly extending spring guide fingers 22 on the jacket head 26, which spring guide fingers extend inwardly into the valve chamber 34. The jacket head has a central discharge outlet 28 and four surrounding, spaced-apart discharge outlets 30 located between the spring guide fingers 22. The jacket head 26 has a threadable, screw-type fastening means 38 on its outer perimeter for threadably securing the head to the threadable screw-type means 36 on the inner perimeter of the end of the valve jacket 18. The four inwardly extending spring guide fingers 22 each have a portion cut out thereon on their inner surface to provide a ball valve stop area 23 for the teflon-coated metal ball 12. The valve jacket 18 has an outwardly, radially extending flange 16 on its outer distal end for retaining the apparatus 10 in a position outside and against the urethral opening of the subject, an elongated cylinder-type valve jacket 18 with a jacket membrane collar 20 to enclose the inflatable collar membrane 24, and a rounded end surface 44 to provide a comfortable fit for the subject within the urethra. A fluid pump valve 32 is shown on the outer surface of the flange 16 to provide for inflation of the inflatable collar membrane 24 after the apparatus 10 is inserted within the urethra to secure and stabilize the apparatus against the urethral wall.

Figure 2:
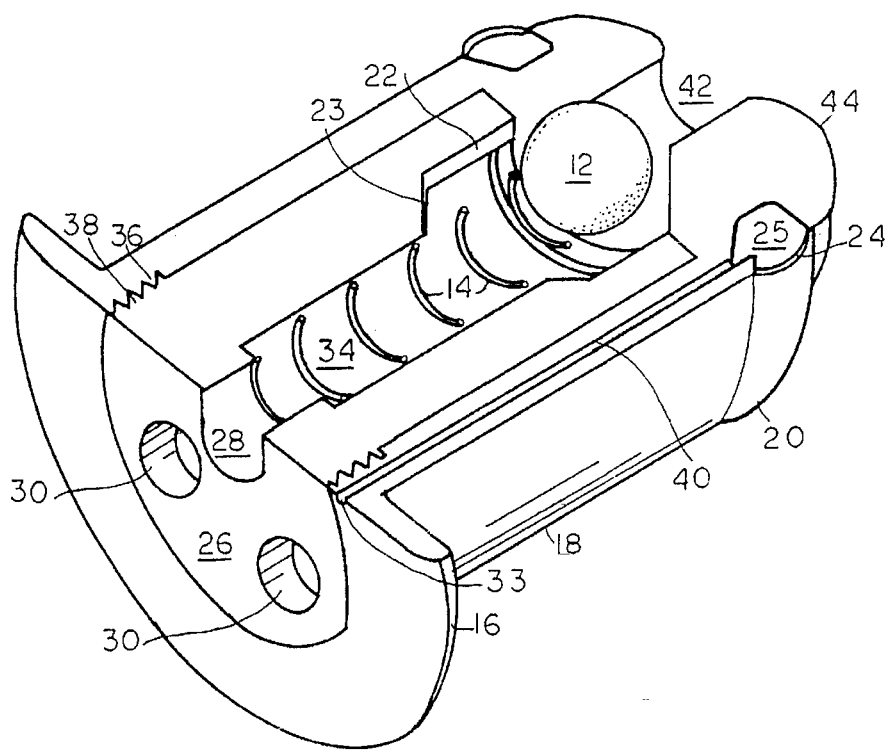
FIG. 2 is partially sectional, perspective view of the urine control valve of FIG. 1.

FIG. 2 is a cutaway, perspective, sectional view of the assembled involuntary urine control apparatus of the invention 10 with the teflon-coated metal ball 12 resting on the tension-biased spring 14 within the spring guide fingers 22 on the jacket head 26. The drawing further depicts the head and jacket thread areas 36 and 38 for the threadable, removable securing of the jacket head 26 to the valve jacket 18, and also shows the central discharge passageway outlet 28 and two of the spaced apart discharge chamber outlets 30. The outer flange 16 of the apparatus is shown with an opening 33 for the valve capillary tube passageway 40 leading to the inflatable collar membrane chamber 25, which membrane chamber 25 is surrounded by a collar membrane 24 and is shown in its inflated form, creating the slightly diameter-enlarged jacket collar 20 to stabilize the apparatus 10 within the urethra. The valve jacket 18 is illustrated with the rounded end 44 and the urethral discharge passageway inlet 42 leading to the chamber passageway 34.

Figure 3:
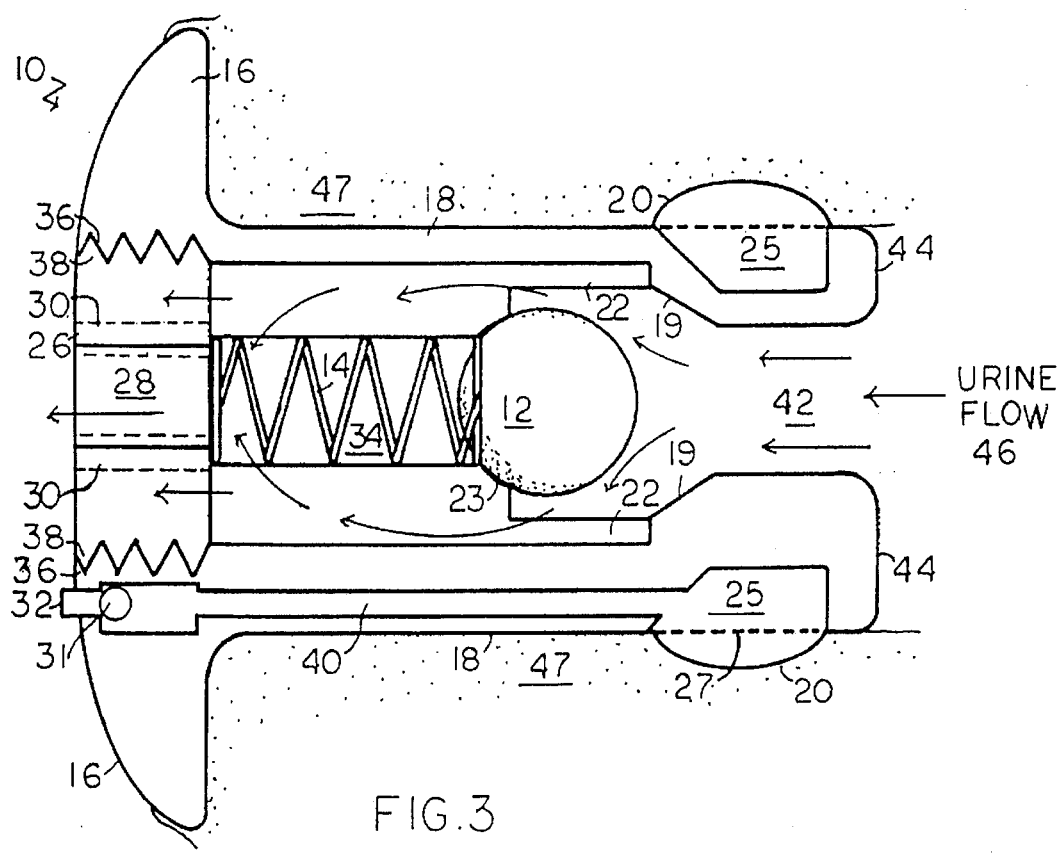
FIG. 3 is a sectional view of the urine control valve of FIG. 2 with the ball valve in the urine flow position.

FIG. 3 is an enlarged, side sectional view of the involuntary urine control apparatus of the invention 10 in the open, urine flow position, with the teflon-coated metal ball 12 resting against the ball valve stop 23 created by the inwardly extending spring guide fingers 22, the ball held in this position by means of a magnet, employed by the subject, being placed adjacent the control apparatus means, permitting the magnetic field of the magnet means to activate the magnetically-activated ball valve means and moving the ball 12 away from the ball valve seat 19 to the open position as desired. The urine flow 46 is now able to enter the central discharge passageway 42 and flow out of the control valve 10 through the central discharge passageway outlet 28 and the surrounding, spaced apart discharge outlets 30 located in the jacket head 26. The jacket head 26 is secured to the valve jacket 18 by a threadable screw-type means 38 threaded to the jacket threadable screw-type means 36;, and the jacket collar 20 is shown in its inflated condition, having been inflated by air entering the pump 32 and passing through the valve capillary tube passageway 40, with the inflatable collar membrane 24 resting in a secure manner against the urethral wall 47. The position of the collar membrane 24 when it is in the deflated condition 27 is indicated in dotted lines.

The outer flange 16 retains the apparatus 10 in a secure manner against the subject's urethral opening, and at the other end the rounded end 44 of the valve jacket 18 provides for comfortable insertion and withdrawal of the apparatus 10 within the urethra. The jacket collar 20 can also be deflated by means of inserting a rod or pin into the valve pump 32, and dislodging the check ball 31 within the valve to allow fluid to escape the valve pump 32.

Figure 4:
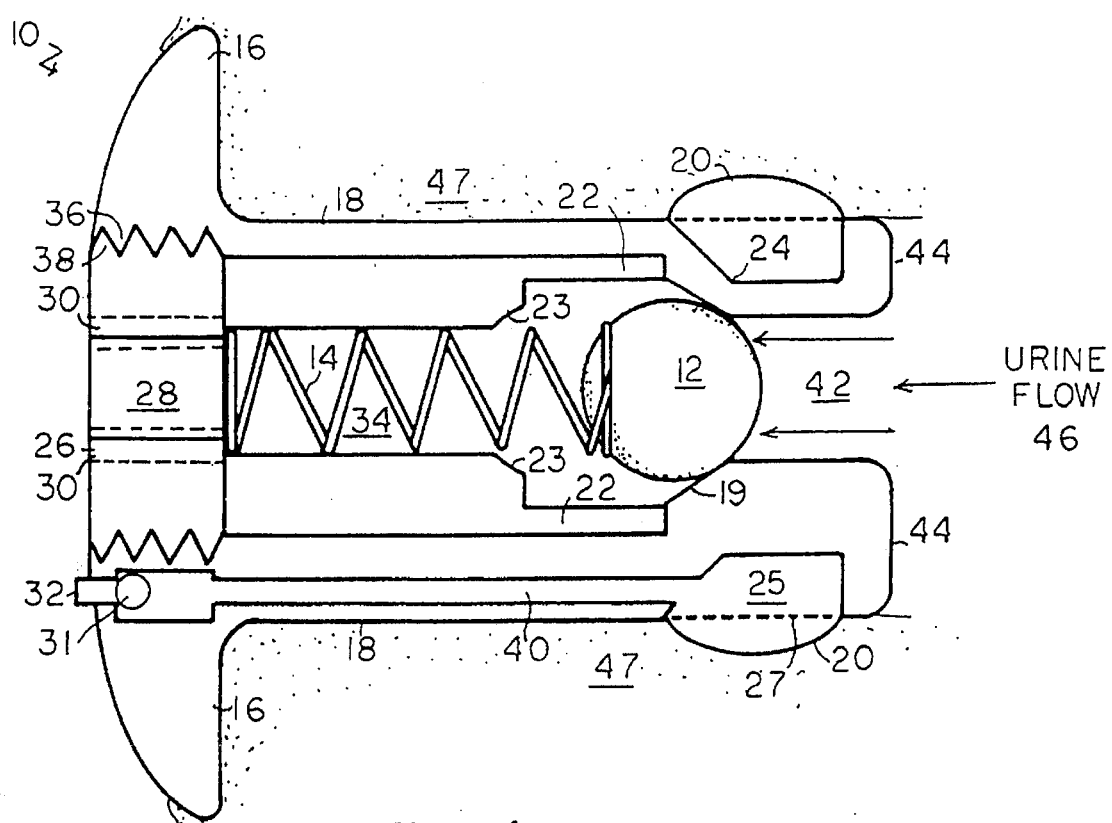
FIG. 4 is a sectional view of the ball valve of FIG. 2 with the ball valve in the urine stop position.

FIG. 4 is an enlarged, side sectional view of the involuntary urine control apparatus of the invention 10 in a closed, non-urine flow position, with the teflon-coated metal ball 12 resting against the ball valve seat 19 of the jacket 18 by means of the tension-biased spring 14, which spring at the other end is resting against the jacket head 26 within the spring guide fingers 22. The slightly diameter-enlarged jacket collar 20 is shown in its inflated condition, the collar membrane chamber 25 having been inflated by air entering the valve pump 32 and passing through the valve capillary tube passageway 40, with the inflatable collar membrane 24 resting in a secure manner against the urethral wall 47. Urine flow 46 is prevented from entering the discharge chamber passageway 34 and out the discharge passageway outlets 28 and 30 by the tension-biased metal ball 12 held tensionally against the ball valve seat 19. The outer flange 16 retains the apparatus 10 in a secure manner against the subject's urethral opening, and at the other end the rounded end 44 of the jacket 18 provides for comfortable insertion and withdrawal of the apparatus 10 within the urethra. The jacket collar 20 can also be deflated by means of inserting a rod or pin into the valve pump 32, and dislodging the check ball 31 within the valve to allow fluid to escape the valve. The position of the collar membrane 24 when it is in the deflated condition 27 is indicated in dotted lines.

Figure 5:
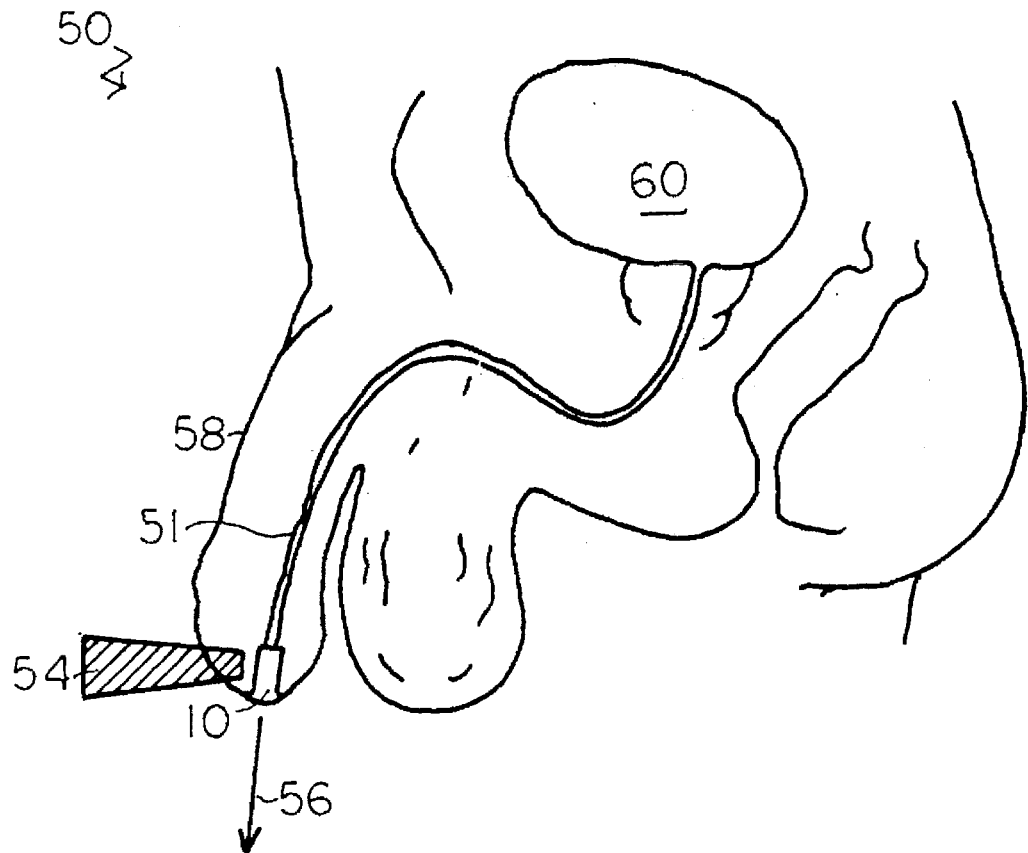
FIG. 5 is a schematic illustration of the urine control valve of the invention in use.

FIG. 5 is a schematic view of the involuntary urine control device of the invention 10 in use in a subject 50, here illustrated as a male subject, with the apparatus 52 inserted within the urethra 51 at the end of the penis 58, with the bladder 60 being emptied by means of the magnet 54 placed in a proximal manner to the apparatus 10, opening the valve to allow for urine flow 56 out of the penis 58.

Figure 6:
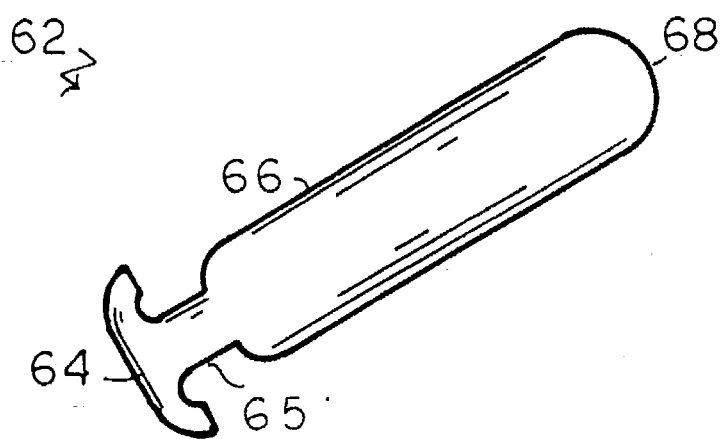
FIG. 6 is a side elevational view of one of the dowels of the urethra tool measuring kit of the invention.

FIG. 6 is a side elevational view of the measuring dowel tool of the invention 62, having a cylindrical shape with a tool body 66 having smooth, rounded sides and a smooth, rounded end 68 to provide for comfort of the subject when inserting and withdrawing the measuring dowel, and a flange element 64 at the outer end for grasping by the user while inserting or withdrawing the measuring tool from the urethra. The flange element 64 is connected to the tool body 66 by means of a neck 65 of lesser diameter than the tool body. The measuring kit, including the measuring dowel tools 62, has a plurality of measuring dowel tools with the body 66 having different, selected diameters to allow for measuring of the urethra to provide for the proper fit of the apparatus within the subject during use. Below is a diagram of the various diameters of the 18 dowels as typically included in the measuring kit:

| Number | Diameter | Number | Diameter |
| --- | --- | --- | --- |
| 1 | .250 | 10 | .295 |
| 2 | .255 | 11 | .300 |
| 3 | .260 | 12 | .305 |
| 4 | .265 | 13 | .310 |
| 5 | .270 | 14 | .315 |
| 6 | .275 | 15 | .320 |
| 7 | .280 | 16 | .325 |
| 8 | .285 | 17 | .330 |
| 9 | .290 | 18 | .335 |

In operation, the involuntary urine control apparatus of the invention comprises an outer valve jacket 18 comprising a radially outwardly-extending flange 16 at one end, a smooth, rounded, outwardly-curved end 44 at the other end, this end having a urine discharge passageway inlet 42 in the middle thereof for the entry of urine to be discharged, and an elongated, cylindrical valve jacket 18 between the inlet and outlet to contain the metal ball 12, tension-biased spring 14 and spring guide fingers 22 of the apparatus 10. The valve jacket 18 has an outer membrane 24 with an inflatable collar means 20 extending in a slightly diameter-enlarged manner around the outer perimeter toward the rounded end 44 to provide for securing and stabilizing the apparatus 10 inside the urethra against the urethral walls 47 when the collar 20 is inflated. The inflatable collar membrane 24 may be inflated by means of a valve pump 32 pumping fluid, such as a gas or liquid, into the valve capillary tube passageway 40 by the subject until the collar membrane chamber 25 is inflated to a desired point; that is, until the apparatus is secured and stabilized against the walls of the urethra. The outer flange means 16 provides for the retaining of the apparatus against the outside of the subject's urethral opening, preventing the apparatus 10 from sliding within the urethra, and the smooth, curved inner end 44 is shaped thus to provide for comfort of the subject during insertion, withdrawal and use.

After the apparatus 10 is inserted and secured within the subject's urethra, the teflon-coated metal ball 12 rests in a tension-biased condition against the ball valve seat 19 preventing the flow of urine into the discharge chamber passageway 34. When desired by the subject, a magnet is held adjacent the apparatus from the outside of the subject's body, to move the ball downwardly against the spring until it rests against the ball valve stop 23 inside the spring guide fingers 22 within the valve jacket 18. In this open position, the urine flow proceeds through the discharge chamber passageway 34, the central 28 and surrounding 30 discharge passageways outlets and out of the jacket head 26. When the bladder is emptied, the subject simply moves the magnet away from the apparatus and the ball 12 is released from the magnetic force and returned to its stop position against the ball valve seat 19, preventing any further urine flow.

It should be noted that if there is sufficient pressure from the urine stored in the bladder exerted on the magnetic ball 12, the ball will move down To allow for the flow of the urine to prevent harmful backup of urine within the urethra. Further, the jacket collar 20, being snug-fit against the urethral wall, prevents any leakage from the bladder between the valve apparatus and the urethral wall.

Thus, the involuntary urine control apparatus of the invention as shown and described provides for an improved method of elimination for subjects with urinary incontinence that is simple and more easily installed and maintained by the subject user.

What is claimed is:

1. An involuntary urine control valve apparatus, which apparatus comprises:

a) a cylindrical jacket having a one outlet end and an other inlet end and an external diameter and surface adapted to fit slidably and comfortably in a snug fit and having a length to be inserted only a short distance into the open distal end of the urethra of a subject;

b) a collar chamber means extending circumferentially about the external diameter of and toward the other inlet end of the jacket;

c) a collar means about the collar chamber means to stabilize the jacket in position within and to the interior wall of the urethra, the collar means adapted to move between a radially outwardly extended, inflated position to stabilize the jacket against the internal wall of the urethra and a radially deflated position to permit the insertion into or removal from the urethra of the jacket;

d) a radially extended flange means having an external surface from the one end of the jacket adapted to fit about and adjacent the open distal end of the urethra;

e) a valve means on the external surface of the flange means to permit the introduction of a fluid into the collar means and to permit the release of the fluid from the collar means;

f) a valve chamber means in the jacket to connect the valve means with the collar means;

g) a head means secured to the outlet end of the jacket and having at least one urine flow passageway to permit the flow of urine externally from the subject;

h) a tension-biased, magnetically activated ball valve within the jacket, which ball valve is adapted to move generally longitudinally within the jacket between a tension-biased closed position against a valve seat to prevent the flow of urine through the jacket from the inlet to the passageway and a magnetically activated, open position with the ball valve removed from the valve seat to permit the flow of urine from the inlet to the passageway, by the external use of a magnet by the subject, the ball valve having sufficient tension to be placed in the closed position, but insufficient to prevent the ball valve to move to the open position unless magnetically activated.

2. The apparatus of claim 1 wherein the valve chamber means comprises a generally longitudinal passageway in the jacket from the valve means to the collar means.

3. The apparatus of claim 1 wherein the tension-biased ball valve comprises a longitudinal spring within the jacket and a metal ball valve having a polymeric coating and positioned at one end of the spring to move between a closed position and an open position.

4. The apparatus of claim 1 wherein the jacket includes a ball valve seat for the tension-biased ball valve about the inlet or outlet of the jacket.

5. The apparatus of claim 1 wherein the flange means comprises a smooth, arcuate surface on the external surface adapted to fit the tissue contour surrounding the end of the urethra.

6. The apparatus of claim 1 wherein the collar means is positioned toward the other inlet end of the jacket and in the deflated position the collar means has a diameter of about the external diameter of the jacket.

7. The apparatus of claim 1 wherein the collar chamber means comprises a portion of the jacket surface.

8. The apparatus of claim 1 wherein the head means is removably secured in the one outlet end of the jacket.

9. The apparatus of claim 8 wherein the head means is threadably secured in the one outlet end of the jacket.

10. The apparatus of claim 1 wherein the head means comprises a central urine flow passageway and a plurality of surrounding spaced-apart urine flow passageways.

11. The apparatus of claim 1 wherein the head means is removably secured within the one outlet end of the jacket and includes a plurality of inward, slightly tapered generally longitudinal spaced-apart guide fingers, within the jacket and about a spring-biased ball valve.

12. An involuntary urine control system which includes the urine control valve of claim 1, and which system includes an external magnet to be employed by a subject to activate the tension-biased ball valve to the open position.

13. The system of claim 12 which includes a finger operated pump to be employed by a subject to inflate the collar means and to stabilize the jacket in position within the urethra.

14. The apparatus of claim 1 wherein the jacket has a length of up to about one inch.

15. The apparatus of claim 14 wherein the one outlet end and the other inlet end are longitudinally aligned and the jacket includes opposite spaced-apart tapered surfaces or valve ball seats internally to permit the ball valve to move between said seats in the closed and open position.

16. The apparatus of claim 1 wherein the collar chamber means defines a circumferential chamber with opposite spaced-apart outer edges on the external diameter of the jacket and the collar means comprises a membrane material extending across the chamber and secured to said opposite outer edges.

17. An involuntary urine control valve apparatus, which apparatus comprises:

a) a cylindrical jacket having a one outlet end and an other inlet end longitudinally aligned and an external diameter and surface adapted to fit slidably and comfortably in a snug fit and having a length to be inserted only a short distance into the open distal end of the urethra of a subject;

b) a collar chamber means extending circumferentially about the external diameter of and toward the other inlet end of the jacket;

c) a collar means about and secured to the collar chamber means to stabilize the jacket in position within and to the interior wall of the urethra, the collar means adapted to move between a radially outwardly extended, inflated position to stabilize the jacket against the internal wall of the urethra and a radially deflated position to permit the insertion into or removal from the urethra of the jacket;

d) a radially extended flange means having an external surface and a smooth, internal surface, from the one end of the jacket adapted to fit about in a contoured manner and adjacent the open distal end of the urethra;

e) a valve means on the external surface of the flange means to permit the introduction of a fluid into the collar means to stabilize the jacket in position within the urethra and a further means to permit the release of the fluid from the collar means;

f) a valve chamber means comprising a generally longitudinal passageway in the jacket to connect the valve means with the collar means;

g) a head means threadably and removably secured to the one outlet end of the jacket and having a plurality of surrounding, spaced-apart urine flow passageways to permit the flow of urine externally from the subject;

h) a tension-biased, magnetically activated ball valve comprised of a metal ball having a thin polymeric coating, which ball valve is adapted to move generally longitudinally within the jacket between a tension-biased closed position against a ball valve seat to prevent the flow of urine through the jacket from the inlet to the passageway and a magnetically activated, open position with the ball valve removed from the valve seat to permit the flow of urine from the inlet to the passageway, by the external use of a magnet by the subject, the ball valve having sufficient tension to be placed in the closed position, but insufficient to prevent the ball valve to move to the open position unless magnetically activated.

18. An involuntary urine control system to control the flow of urine from a subject which includes the apparatus of claim 17, and which system includes:

a) an external magnet to be employed by the subject to activate the tension-biased ball valve to the open position; and b) a finger operated pump to be employed by the subject to inflate the collar means and to stabilize the jacket in position within the urethra.

19. An involuntary urine control valve method, which method comprises:

a) inserting a cylindrical jacket, having a one outlet end and an other inlet end and an external diameter and surface, slidably and comfortably in a snug fit a short distance into the open distal end of the urethra of a subject;

b) stabilizing the jacket in position within and against the interior wall of the urethra with a collar means about the jacket, the collar means moving between a radially outwardly extended, deflated position against the internal wall of the urethra to stabilize the jacket in a use position in the urethra and a radially deflated position of about the external diameter of the jacket to permit the insertion into or removal from the urethra of the jacket by a subject;

c) fitting about and adjacent to the open distal end of the urethra one radially extending flange means having an external surface extending from the one outlet end of the jacket;

d) introducing a fluid into the collar means and permitting the release of fluid from the collar means by a valve means on the external surface of the flange means;

e) connecting the valve means to the collar means with a fluid chamber means in the jacket;

f) securing a head means to the one outlet end of the jacket and having at least one urine flow passageway therein to permit the flow of urine externally from the subject;

g) positioning a tension-biased, magnetically activated ball valve within the jacket, the ball valve adapted to move generally longitudinally within the jacket between a tension-biased closed position against a ball valve seat in the jacket to prevent the flow of urine through the jacket from the inlet to the passageway and a magnetically activated, open position with the ball valve removed from the valve seat permitting the flow of urine from the inlet to the passageway by the external use of a magnet by the subject; and h) employing an external magnet means by a user to move the ball valve between a closed position and an open position.

20. The method of claim 19 which includes periodically deflating the collar means to the deflated position by the valve means to permit the subject to insert or remove the device from the urethra.

21. The method of claim 19 which includes inserting the device a short distance within the urethra of up to about one inch.

22. The method of claim 19 which method includes:

a) providing a central longitudinally aligned urine flow passageway in the head means; and b) providing a plurality of spaced-apart urine flower passageways in the head means about said central urine flow passageway.

23. The method of claim 19 which includes inflating and deflating the collar means positioned in and from a chamber collar means which extends circumferentially about the external diameter of the jacket toward the other inlet end.

* * * * *